(12) United States Patent
Bayha et al.

(10) Patent No.: US 7,235,786 B2
(45) Date of Patent: Jun. 26, 2007

(54) SENSOR FOR DETECTING FOG-LIKE MEDIA

(75) Inventors: Heiner Bayha, Vaihingen/Enz (DE); Jürgen Nies, Pforzheim (DE); Thomas Schuler, Wiernsheim (DE)

(73) Assignee: Valeo Schalter und Sensoren GmbH, Bietigheim-Bissingen (DE)

( * ) Notice: Subject to any disclaimer, the term of this patent is extended or adjusted under 35 U.S.C. 154(b) by 289 days.

(21) Appl. No.: 10/511,901

(22) PCT Filed: Jan. 16, 2004

(86) PCT No.: PCT/EP2004/000290

§ 371 (c)(1),
(2), (4) Date: Oct. 20, 2004

(87) PCT Pub. No.: WO2004/068122

PCT Pub. Date: Aug. 12, 2004

(65) Prior Publication Data

US 2005/0253070 A1    Nov. 17, 2005

(30) Foreign Application Priority Data

Jan. 25, 2003    (DE) ............................... 103 02 970

(51) Int. Cl.
*G01J 5/02* (2006.01)
*G01J 5/00* (2006.01)

(52) U.S. Cl. ............................... 250/339.11; 250/338.1
(58) Field of Classification Search ........... 250/339.11, 250/338.1
See application file for complete search history.

(56) References Cited

U.S. PATENT DOCUMENTS

| | | | | |
|---|---|---|---|---|
| 3,758,211 A | * | 9/1973 | Bateman et al. | 356/340 |
| 4,659,922 A | | 4/1987 | Duncan | |
| 5,254,853 A | * | 10/1993 | Reich | 250/221 |
| 6,144,022 A | * | 11/2000 | Tenenbaum et al. | 250/208.1 |
| 6,422,062 B1 | * | 7/2002 | King et al. | 73/29.01 |
| 6,495,815 B1 | * | 12/2002 | Stam et al. | 250/208.1 |
| 2002/0156559 A1 | * | 10/2002 | Stam et al. | 701/36 |

FOREIGN PATENT DOCUMENTS

| | | | |
|---|---|---|---|
| DE | 43 26 170 | | 2/1995 |
| DE | 4326170 | * | 2/1995 |
| DE | 196 29 712 | | 1/1998 |
| FR | 2 584 497 | | 1/1987 |

* cited by examiner

Primary Examiner—David Porta
Assistant Examiner—David S. Baker
(74) Attorney, Agent, or Firm—Paul Vincent

(57) ABSTRACT

The invention relates to a sensor for detecting fog-like media, comprising at least two emitters and at least one receiver, whereby the emission axes intersect with the receiver axis at two different positions. The inventive sensor also comprises an evaluation unit that detects the medium when the receiver receives signals emitted by both emitters.

28 Claims, 2 Drawing Sheets

SENSOR FOR DETECTING FOG-LIKE MEDIA

This application is the national stage of PCT/EP2004/000290 filed on Jan. 16, 2004 and also claims Paris Convention priority of DE 103 02 970.2 filed on Jan. 25, 2003.

BACKGROUND OF THE INVENTION

The invention concerns a sensor for detecting fog-like media. Fog-like media are e.g. fog, mist, vapor, smoke or the like. The invention also concerns a method for detecting such fog-like media.

Sensors and methods of this type may be used, in particular in automotive technology, to increase the safety standard of vehicles. The sensors and methods may be used e.g. for automatic switching on and off or control of fog lights of a vehicle, for issuing a warning to the driver or for automatic speed adjustment in dependence on the weather conditions.

The detection of fog-like media is problematic, since these media are generally translucent.

It is therefore the underlying purpose of the present invention to provide a sensor which is suited for detecting fog-like media and also a method for detecting fog-like media.

SUMMARY OF THE INVENTION

This object is achieved with a sensor comprising at least two transmitters and at least one receiver, wherein the transmitter axes and the receiver axis intersect at two different positions, and with an evaluation unit which detects the medium when the receiver detects signals transmitted by both transmitters.

This object is also achieved by a sensor comprising at least one transmitter and at least two receivers, wherein the transmitter axis and the receiver axes intersect at two different positions, and with an evaluation unit which detects the medium when the two sensors receive signals transmitted by the transmitter.

The inventive sensor checks, at at least two different positions, whether transmitted signals are reflected by the fog-like medium and therefore whether or not fog-like media are present. The presence of such fog-like media produces spatial reflection. If no media are present, no reflection occurs. If there is a massive object which cannot be spatially penetrated by light, there is generally no reflection at the detected positions. The surface of an object which cannot be penetrated by light is neither at the one nor at the other position. The transmitted signals may be reflected at either one or the other position, if at all, depending on the position of the object. However, reflection at both positions is impossible.

The inventive sensors are therefore suited to detect fog-like media in a simple manner.

The inventive sensors preferably comprise an optics which focuses the signals to be transmitted or received along a respective, preferably largely cylindrical or linear beam and along the respective transmitter or receiver axis. This is advantageous in that the positions at which the axes intersect subtend a relatively small volume thereby providing a relatively precise measurement.

In one advantageous embodiment, the two transmitter axes or the two receiver axes extend largely parallel to each other. The two receiver axes or the two transmitter axes should not intersect each other.

An advantageous sensor is characterized in that the evaluation unit is suited to determine the density of the medium to be detected on the basis of a comparison of the intensity of the signals to be transmitted and of the intensity of the signals to be received. The properties of the medium can be detected by comparing the intensities of the transmitted and received signals. In case of dense fog, the intensity of the receiving signals is different from that of less dense fog.

An advantageous sensor can be obtained if the transmitter is an infrared transmitter and the receiver is an infrared receiver.

In particular, if the sensor is used for a vehicle, it is advantageous that the sensor be suitable for mounting to a window, in particular to the windshield of a vehicle.

To optimally reduce the signal loss, a coupling means may be provided between the optics and the window. To obtain a compact sensor, the at least one transmitter and/or the at least one receiver may be disposed on a circuit board. It may also be advantageous to dispose the evaluation unit on this circuit board.

The inventive sensor preferably generates a signal for controlling a system to detect fog. Such a system may e.g. be the fog lights of a vehicle, i.e. the fog lights are automatically activated upon detection of fog-like media or are deactivated if fog-like media are no longer detected. Moreover, a warning signal may be issued to the driver in the form of an optical, acoustic or tactile signal, to draw his/her attention to the accumulating fog.

The above-mentioned object is also achieved by a method for detecting fog-like media which is characterized in that signals are transmitted by at least two transmitters, wherein a receiver axis of a receiver intersects the two transmitter axes at different positions and subsequently detects the medium when the receiver receives the signals transmitted by both transmitters.

The above-mentioned object is also achieved by a method which is characterized in that signals are transmitted by at least one transmitter, wherein at least two receiver axes, each associated with one receiver, intersect the transmitter axis at different positions and the medium is subsequently detected when the receivers receive signals transmitted by the transmitter.

The density of the medium can advantageously be determined by comparing the intensity of the transmitted signals and of the intensity of the received signals.

The method is advantageous when the transmitter or the transmitters transmit(s) signals with a time delay and/or alternately. This permits association of the transmitted signals with the received signals.

The inventive method advantageously also concerns infrared signals.

The method transmits a signal when the medium is detected which permits control of e.g. the fog lights of a vehicle or a warning signal.

Further advantageous details and embodiments of the invention can be extracted from the following description which further describes and explains the invention on the basis of the embodiments shown in the drawing.

DESCRIPTION OF THE PREFERRED EMBODIMENT

Figure 1:
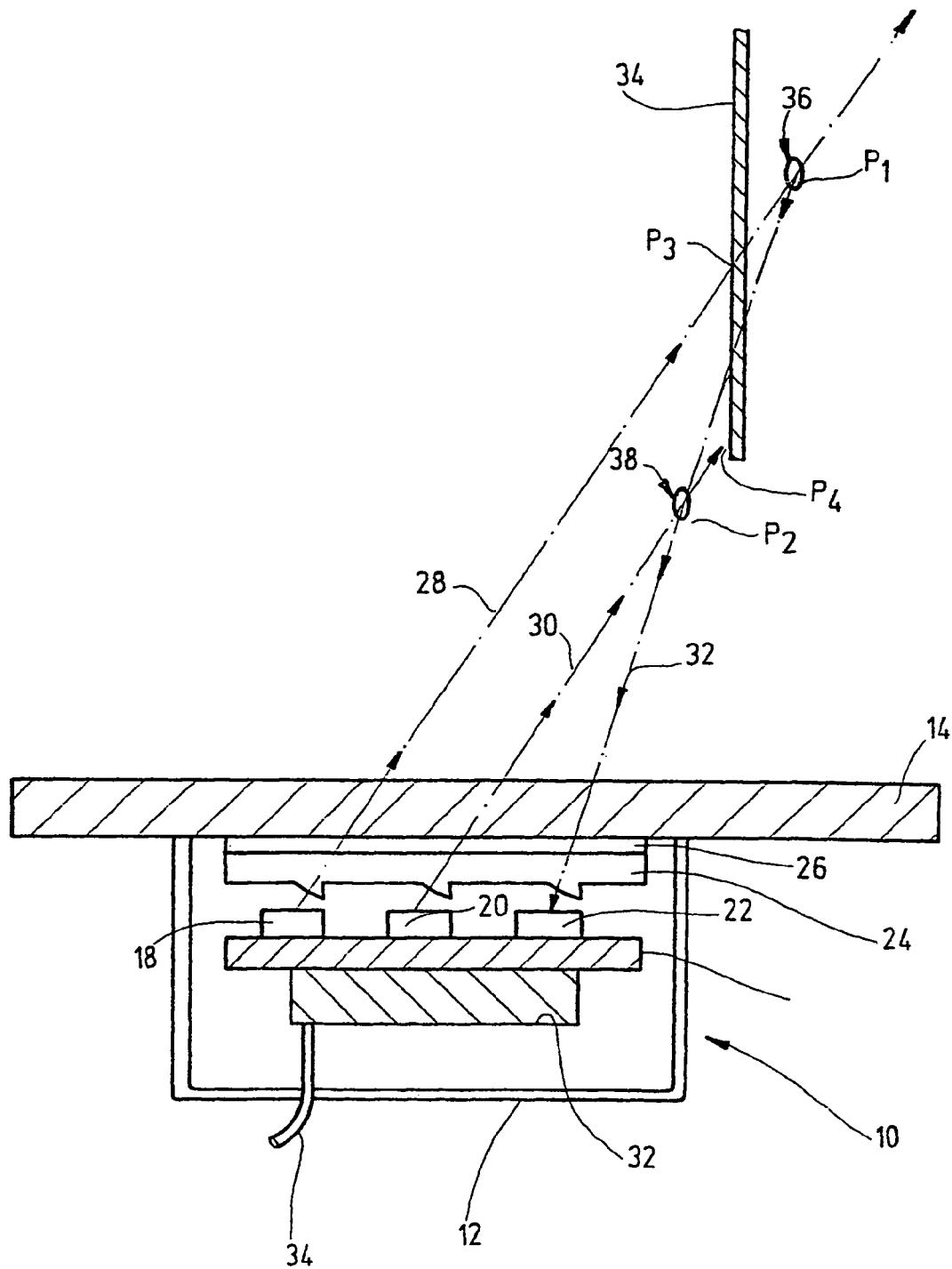
FIG. 1 shows a schematic view of a first inventive sensor.

FIG. 1 shows a sensor 10 for detecting fog which is disposed, with a housing 12, on the inner side of a vehicle window 14. The sensor 10 comprises a board 16 on which two transmitters 18, 20 and one receiver 22 are disposed. On the side facing the window 14, the sensor 10 comprises an optics 24 and a coupling layer 26 disposed between the optics 24 and the window 14.

The optics 24 is designed to focus the infrared signals transmitted by the transmitters 18, 20 along a preferably largely linear beam 28, 30. In the sensor 10 shown in the figure, the axes directions of the beams 28, 30 are largely identical.

The optics 24 moreover directs the signals to be received by the receiver 22 to substantially lie along a straight beam 32.

The two beam paths 28, 30 are parallel (FIG. 1). The beam path 32 intersects the two beam paths 28, 30 at two different positions $P_1$ and $P_2$. All beam paths 28, 30, 32 are therefore co-planar.

The sensor 10 also includes an evaluation unit 32 which detects fog when the receiver 22 receives signals transmitted by both transmitters 18, 20, which are reflected by fog particles 36, 38 at positions $P_1$ and $P_2$. Due to the presence of fog particles in space, the reflection does not occur at a defined border layer, but is distributed in space, along the transmitter axes 28, 30, i.a. also at positions $P_1$ and $P_2$.

If a body which cannot be spatially penetrated by light (indicated in FIG. 1 by reference numeral 34) is located in the region of the sensor 10, this body 34 is reflected at points $P_3$ and $P_4$. Since the points $P_3$ and $P_4$ are not on the receiver axis 32, the receiver 22 receives no signals. Only if fog-like media are present in the detection range of the sensor 10, are the signals transmitted by the transmitters 18, 20 detected by the receiver 22.

The signals transmitted by the transmitters 18, 20 are preferably transmitted with a time delay or alternately which provides information concerning whether the signals received by the receiver 22 have come from the transmitter 18 or transmitter 20.

Of course, in accordance with the invention, more than two transmitters and more than one receiver may be provided in a sensor. Provision of several different positions of intersecting beam paths permits safe and accurate statements about the presence of fog in the detected range.

The sensor 10 is preferably coupled to other vehicle systems via communication means 34. It may e.g. be provided that the fog lights of the vehicle are activated when the fog sensor 10 detects fog. It is also feasible to emit warning signals to the driver in case of fog.

Figure 2:
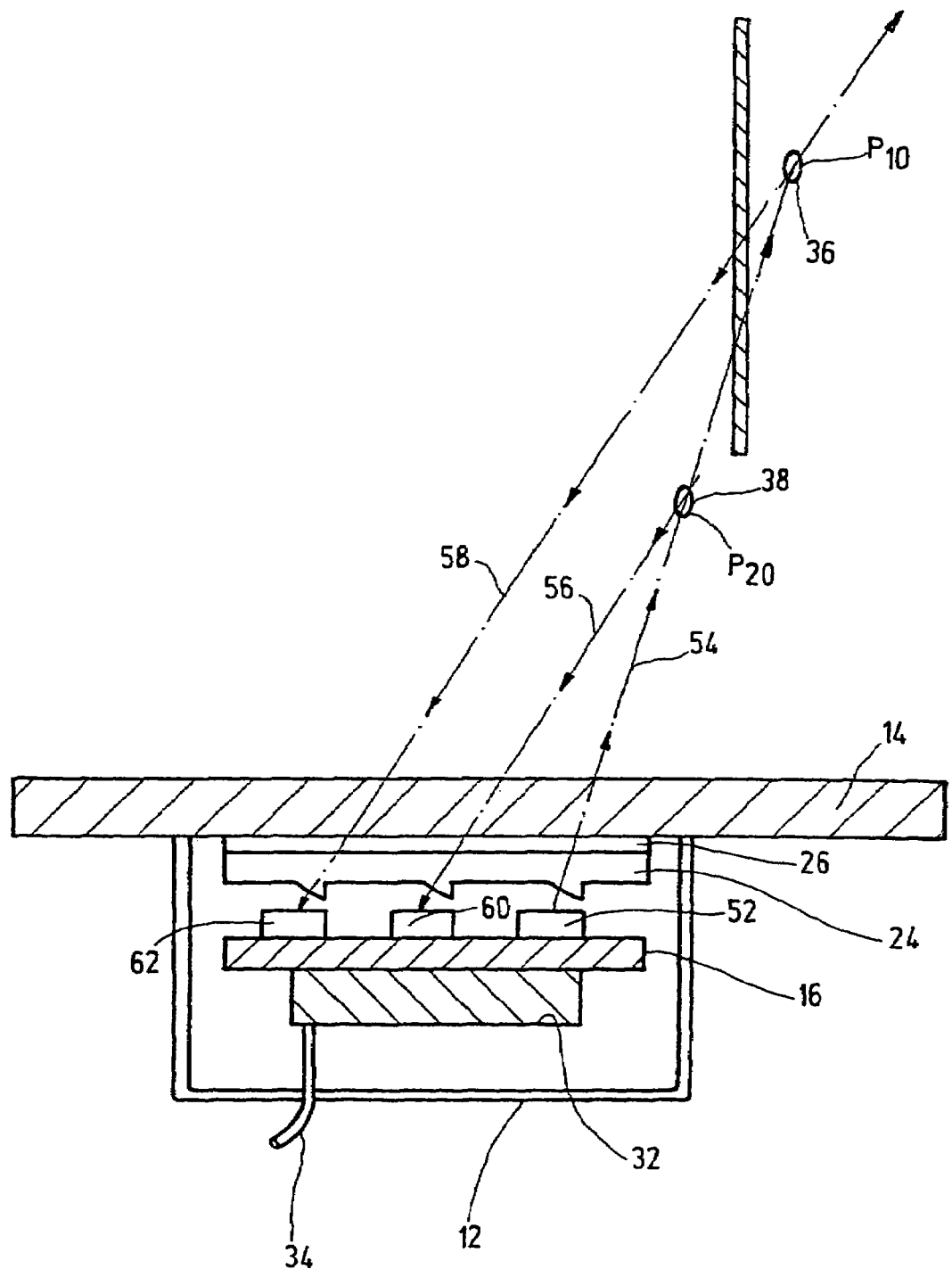
FIG. 2 shows a schematic view of a second inventive sensor.

The sensor 50 shown in FIG. 2 differs from the sensor 10 of FIG. 1 in that signals transmitted by a transmitter 52 along a transmitter axis 54 intersect two receiver axes 56, 58 of two receivers 60, 62 at two different positions $P_{10}$, $P_{20}$. Infrared signals transmitted by the transmitter 52 are detected by the two receivers 60, 62 only when fog-like media are present in the detection range of the sensor 50.

The intensity of the transmitted signals can advantageously be compared with the intensity of the received signals using the evaluation unit 31 to provide information about the density of the detected fog-like medium.

All of the features shown in the description, the following claims and the drawing may be essential to the invention either individually and also collectively in arbitrary combination.

We claim:

1. A sensor for detecting a fog-like medium, the sensor comprising:
   a first transmitter for transmitting first signals along a first transmission axis and towards the fog-like medium;
   a second transmitter for transmitting second signals along a second transmission axis and towards the fog-like medium;
   a receiver for receiving said first and said second signals subsequent to interaction with the fog-like medium, said receiver receiving said first and said second signals along a receiver axis, wherein said receiver axis intersects said first transmission axis at a first point of intersection and said receiver axis intersects said second transmission axis at a second point of intersection; and
   an evaluation unit communicating with said receiver to detect the medium in response to reception of said first and said second signals, wherein said first and said second transmission axis do not intersect.

2. The sensor of claim 1, further comprising a first optics to focus said first signals emanating from said first transmitter into a first beam travelling along said first transmission axis, a second optics to focus said second signals emanating from said second transmitter into a second beam travelling along said second transmission axis, and a third optics to select portions of said first and said second signals which travel toward said receiver along said receiver axis and to pass said selected portions on to said receiver.

3. The sensor of claim 2, further comprising means for mounting the sensor to a window or a windshield.

4. The sensor of claim 3, further comprising optical coupling means disposed between said window or windshield and at least one of said first optics, said second optics, and said third optics.

5. The sensor of claim 2, wherein said first beam, said second beam and said selected portions each form substantially cylindrical, linear beams.

6. The sensor of claim 1, wherein said first and said second transmission axes are substantially parallel to each other.

7. The sensor of claim 1, wherein said evaluation unit is adapted to determine a density of the medium by comparing received intensities of said first and said second signals with transmitted intensities of said first and said second signals.

8. The sensor of claim 1, wherein said first and said second transmitters are infrared transmitters and said receiver is an infrared receiver.

9. The sensor of claim 1, further comprising a circuit board on which at least one of said first transmitter, said second transmitter, and said receiver are disposed.

10. The sensor of claim 1, wherein the sensor is adapted to generate a signal for controlling a system to detect a fog-like medium.

11. A method for detecting a fog-like medium, the method comprising the steps of:
   a) transmitting first signals along a first transmission axis and towards the fog-like medium;
   b) transmitting second signals along a second transmission axis and towards the fog-like medium, wherein said first and said second transmission axes do not intersect;
   c) receiving said first and said second signals along a receiver axis and subsequent to interaction with the fog-like medium, wherein said receiver axis intersects said first transmission axis at a first point of intersection and said receiver axis intersects said second transmission axis at a second point of intersection; and d) communicating with said receiver to detect the medium in response to reception of said first and said second signals.

12. The method of claim 11, further comprising determining a density of the medium by comparing an intensity of transmitted signals to an intensity of received signals.

13. The method of claim 11, further comprising time delaying or alternating said first signals with respect to said second signals.

14. The method of claim 11, wherein said first and said second signals are infrared signals.

15. The method of claim 11, wherein a signal is issued when the medium is detected.

16. A sensor for detecting a medium, the sensor comprising:
  a transmitter for transmitting signals along a transmission axis and towards the fog-like medium;
  a first receiver for receiving said signals subsequent to interaction with the fog-like medium, said first receiver receiving said signals along a first receiver axis, wherein said first receiver axis intersects said transmission axis at a first point of intersection;
  a second receiver for receiving said signals subsequent to interaction with the fog-like medium, said second receiver receiving said signals along a second receiver axis, wherein said second receiver axis intersects said transmission axis at a second point of intersection;
  an evaluation unit communicating with said first and said second receivers to detect the medium in response to reception of said signals in said first and said second receivers;
  a first optics to focus said signals emanating from said transmitter into a first beam travelling along said transmission axis;
  a second optics to select first portions of said signals which travel toward said first receiver along said first receiver axis and to pass said selected first portions on to said first receiver;
  a third optics to select second portions of said signals which travel towards said second receiver along said second receiver axis and to pass said selected second portions on to said second receiver;
  means for mounting the sensor to a window or a windshield; and
  optical coupling means disposed betwen said window or windshield and at least one of said first opticl, said second optics, and said third optics.

17. The sensor of claim 16, wherein said first and said second receiver axes do not intersect.

18. The sensor of claim 17, wherein said first and said second receiver axes are substantially parallel to each other.

19. The sensor of claim 16, wherein said first beam, said first portions and said second portions each form substantially cylindrical, linear beams.

20. The sensor of claim 16, wherein said evaluation unit is adapted to determine a density of the medium by comparing received intensities of said signals with transmitted intensities of said signals.

21. The sensor of claim 16, wherein said first and said second receivers are infrared receivers and said transmitter is an infrared transmitter.

22. The sensor of claim 16, further comprising a circuit board on which at least one of said transmitter, said first receiver, and said second receiver are disposed.

23. The sensor of claim 16, wherein the sensor is adapted to generate a signal for controlling a system to detect a fog-like medium.

24. A method for detecting a fog-like medium, the method comprising the steps of:
  a) transmitting signals along a transmission axis and towards the fog-like medium;
  b) receiving said signals subsequent to interaction with the fog-like medium along a first receiver axis, wherein said first receiver axis intersects said transmission axis at a first point of intersection;
  c) receiving said signals subsequent to interaction with the fog-like medium along a second receiver axis, wherein said second receiver axis intersects said transmission axis at a second point of intersection; and
  d) detecting the medium in response to reception of said signals, wherein a first optics focuses said signals emanating from said transmitter into a first beam travelling along said transmission axis, a second optics selects first portions of said signals which travel toward said first receiver along said first receiver axis to pass said selected first portions on to said first receiver, and a third optics selects second portions of said signals which travel towards said second receiver along said second receiver axis and passes said selected second portions on to said second receiver, and with means for mounting the sensor to a window or a windshield as well as optical coupling means disposed between said window or windshield and at least one of said first optics, said second optics, and said third optics.

25. The method of claim 24, further comprising determining a density of the medium by comparing an intensity of transmitted signals to an intensity of received signals.

26. The method of claim 24, further comprising time delaying or alternating signals received by said first receiver with respect to signals received by said second receiver.

27. The method of claim 24, wherein said signals are infrared signals.

28. The method of claim 24, wherein a signal is issued when the medium is detected.

* * * * *